United States Patent [19]

Romero-Sierra et al.

[11] 4,328,256
[45] May 4, 1982

[54] PRESERVATION OF GREEN PLANT TISSUES

[75] Inventors: Cesar Romero-Sierra, Bath; John C. Webb, Kingston, both of Canada

[73] Assignee: Queen's University at Kingston, Kingston, Canada

[21] Appl. No.: 271,862

[22] Filed: Jun. 9, 1981

Related U.S. Application Data

[63] Continuation-in-part of Ser. No. 61,688, Jul. 30, 1979, Pat. No. 4,278,715.

[51] Int. Cl.³ .................. A01N 3/00; C09K 15/06
[52] U.S. Cl. .................. 427/4; 252/400 A; 252/407; 252/380; 422/40
[58] Field of Search ........... 427/4; 47/DIG. 2; 71/68; 252/400 R, 400 A, 405, 407; 428/22

[56] References Cited

U.S. PATENT DOCUMENTS

| | | | |
|---|---|---|---|
| 1,484,656 | 2/1924 | Koropp | 47/DIG. 2 |
| 2,567,929 | 9/1951 | Fessenden | 427/4 |
| 2,606,843 | 8/1952 | Fessenden | 427/4 |
| 2,658,836 | 11/1953 | Fessenden | 427/4 |
| 2,698,809 | 1/1955 | Fessenden | 427/4 |
| 3,895,140 | 7/1975 | Sheldon | 427/4 |

*Primary Examiner*—Sam Silverberg
*Attorney, Agent, or Firm*—Richard J. Hicks; Stanley E. Johnson

[57] ABSTRACT

A process for preserving green colored plant tissues and in particular coniferous needles, holly and low fiber leaves such as mosses, lichens and ferns in which selected leaves are immersed in a solution comprising (by volume) 35-45% water, 20-30% 2-propanol, 5-12% propionic acid, 5-10% sulphurous acid, 5-10% formalin, 2.5-5% formic acid, 1-5% ethylene glycol, and optionally minor amounts of compounds selected from the group consisting of cupric sulphate, cupric chloride, 20-20-20 fertilizer, citric acid, DBE, magnesium sulphate, acetic acid, cupric acetate, cupric nitrate, sodium phosphate, sodium sulfite, butylated hydroxytolulene and glycerol, for a sufficient time to exchange the naturally occurring water in the tissues with the "chemical water" of the solution and thereby permanently retain and biologically fix the green color of the leaves.

8 Claims, No Drawings

PRESERVATION OF GREEN PLANT TISSUES

CROSS REFERENCE TO RELATED APPLICATION

This application is a continuation-in-part of our earlier filed U.S. application Ser. No. 61,688 filed July 30, 1979 entitled "Preservation of Green Plant Tissues" and now issued as U.S. Pat. No. 4,278,715.

FIELD OF INVENTION

This invention relates to the preservation of green plant tissues and more particularly to a novel composition of matter for the preservation of the natural green colour in leaves, stems and the like of flowers, shrubs, trees and the like and the preserved product.

BACKGROUND OF INVENTION

In the copending application referred to above, the disclosure of which is incorporated herein by reference, there is described a process and composition of matter for preserving green coloured plant tissue while retaining the natural green colour thereof, in which the tissues are immersed in a solution comprising 30–70% by volume water; at least one monohydric alcohol; at least one preservative component selected from the group comprising lower carboxylic acids, and di and trihydric alcohols, and sufficient buffering and mordant reagents to control the pH and osmolality of the solution so as to permanently retain the green colour in the tissues. Within this general description of the treatment solutions which is suitable for almost all kinds of green leaves, we have found that certain green tissues such as ferns, grasses, lichens, mosses salal, and certain coniferous needles are best treated with modified or special solutions particularly formulated for their special requirements.

BRIEF DESCRIPTION OF INVENTION

By one aspect of this invention there is provided a solution, for the preservation of naturally green coloured plant tissues, consisting essentially of: 35–45% by volume water; 20–30% 2-propanol, 5–12% propionic acid, 5–10% sulphurous acid, 5–10% formalin, 2.5–5% formic acid, 1–5% ethylene glycol, a selected amount of (a) at least one cupric salt selected from the group consisting of cupric sulphate, cupric chloride, cupric carbonate, cupric acetate and cupric nitrate, (b) citric acid, (c) sodium phosphate, (d) sodium sulfite, (e) DBE, (f) 20-20-20 fertilizer, (g) magnesium sulphate (h) glycerol, (i) butylated hydroxytoluene.

By another aspect there is provided a process for preserving naturally green coloured plant tissues comprising immersing said tissues in a solution comprising: 35–45% by volume water; 20–30% 2-propanol; 5–12% propionic acid; 5–10% sulphurous acid; 5–10% formalin; 2.5–5% formic acid; 1–5% ethylene glycol; a selected amount of (a) at least one cupric salt selected from the group consisting of cupric sulphate, cupric chloride, cupric carbonate, cupric acetate and cupric nitrate, (b) citric acid, (c) sodium phosphate, (d) sodium sulphite, (e) DBE, (f) 20-20-20 fertilizer, (g) magnesium sulphate, (h) glycerol, (i) butylated hydroxytoluene.

DETAILED DESCRIPTION

The preservation of green plant tissue specimens is considerably more difficult than preservation of relatively fibrous flowers and the like. Firstly, the cellulose and similar materials in green plant tissues form a relatively rigid framework into which the cells are arranged. The cells are, however, fully turgid only when filled with water and once this water is lost they collapse and the weight of tissues is too great for the relatively small amount of fibre to support. When this happens wilting occurs when the tissue dries out completely, rigidity is restored due to the loss of weight and the loss of lubrication between fibres. In succulents, mosses, ferns and lichens there is so little fibre that complete dehydration and rigidity is almost impossible to achieve. The dehydration process must be complete before the tissue is removed from its physical supporting medium. Failure to ensure this results in loss of shape and chemical reactions which ultimately result in tissue discoloration. Secondly, the green coloration is due to the presence of chlorophyll which is a highly reactive and sensitive substance, and unless considerable care is taken with the dehydration process, degradation of the chlorophyll occurs. It is therefore necessary to effect dehydration in such a way as to retain the original colour and shape substantially intact and subsequently treat the dehydrated tissue with a preservative to make it last.

As discussed in our parent application Ser. No. 61,688 we have found that rather than dehydrate leaves or other green plant tissue and then preserve the dried tissues, it is preferable to effect an exchange process wherein the naturally contained water in the tissue is exchanged with a water based treatment solution containing sufficient chemical reagents to biologically preserve and environmentally fix the green colours. Buffers and the like may be added to modify the effects of the primary chemicals.

Thus, it has been found that a suitable treatment solution for green plant tissues must contain four essential groups of chemicals which may be defined as:
(a) water,
(b) an exchange medium,
(c) preservatives, and
(d) buffers, mordants and modifiers.

Throughout this specification, when referring to "water" it is implicit that distilled water is normally employed, in order to ensure uniformity or results and to provide a readily controlled standard, but it will be appreciated that distillation is not an essential characteristic of the water employed, other forms such as deionized water being equally effective. The "exchange medium" used in the present inventions is normally one or more monohydric alcohols containing 1-6 carbon atoms. Such alcohols, particularly ethyl alcohol, isopropyl alcohol and tertiary butyl alcohol are known to have considerable dehydration properties and, without wishing to be bound by this explanation, it is believed that in the present invention the alcohol or mixtures of alcohols selected causes dehydration of the natural water contained in the plant tissue and the simultaneous replacement thereof by the chemical-containing water of the inventive solutions of the alcohols listed, tertiary butyl alcohol is extremely harsh and may damage leafy tissue and for this reason is normally used in admixture with a milder alcohol such as 1-propanol or 2-propanol. Ethyl alcohol, on the other hand may be used alone.

The preservative elements include biological preservatives and fixers and environmental fixers, such as sulphurous acid.

The buffers, mordants and modifiers include citric acid and cupric salts such as cupric acetate, cupric chloride and cupric sulphate. Minor amounts of other chemicals have been found useful modifiers, including such chemicals as garden fertilizer and in particular 20-20-20 (N-P-K ratio) fertilizer. The amounts of each chemical required depends upon the type of leaf being treated, the exchange medium being used and other factors. Some chemicals appear to act as colour mordants while others are buffers not only for pH but also for osmolality. The pH range is not considered critical and although the bath is generally maintained in the range 6-8, i.e. substantially neutral, pH as low as about 2 may also be employed.

The procedures to be adopted for treatment of the plant tissue are simple and straightforward. Firstly a treating solution is prepared by mixing the required chemicals, preferably in the order as noted below, and then immersing the specimens in the treating solution, at ambient temperature, for 10 days to 2 weeks or even longer depending upon the specimen. For example most deciduous leaves require a relatively shorter period of time than evergreens and thick tough leaves such as holly may require as long as 30 days or even more. Very thick leaves, for example rubber leaves, may require even longer. Leaves of succulents and other species which tend to be very watery and with little fibrous structure (for example water cress) by reason of their species or method of culture are somewhat difficult to treat according to the present invention even if great care is taken with the selection of the exchange medium as it appears difficult to balance the rate of exchange of natural water with the treating solution. Generally, upon immersion in the bath the colour of the leaves changes usually to a lighter green, then as the treatment solution replaces the natural water the colour reverts to an "ideal" colour and on continued immersion the colour darkens. Following treatment in the treating solution, the specimens may be air dried and stored for use as required. Such treated specimens are best used (for teaching or similar purposes) within 2 to 3 weeks as they tend to dry out after that time. If it is desired to preserve the specimens for later use (i.e. spring or summer leaves for use as teaching aids in mid-winter) or for permanent display, a secondary treatment in a "holding solution" is required. The holding solution is a glycerin/water solution preferably containing 100-700 ml glycerin per liter of water. The specimens are merely immersed and soaked in the holding solution for 2-3 weeks, at ambient temperature and then air dried. Specimens so treated maintain their colour and flexibility for periods in excess of 1 year. In certain circumstances it may be desirable to store the specimens permanently in the holding solution, depending on the end use. There is, therefore, no practical limit to the treatment time in the holding solution.

Treatment of forest mosses, lichens, sword ferns, grasses, asparagus ferns, sphagnum mosses, oregon grape, salal and the like present special problems because of their delicate texture and we have found that a solution comprising:
  425 ml distilled water
  14.2 g cupric sulphate
  56 ml propionic acid
  75 ml sulphurous acid
  25 ml formic acid
  100 ml formalin
  80 g cupric chloride
  10 g 20-20-20 N-P-K fertilizer
  42 g citric acid
  2.8 g magnesium sulphate
  25 ml acetic acid
  10 g cupric acetate
  10 g cupric nitrate
  10 g sodium phosphate (dibasic)
  5.6 g sodium sulphite
  238 ml 2-propanol
  0.21 g butylated hydroxytoluene
  42 ml ethylene glycol
  14 ml glycerol
is particularly suitable.

Salal may also be effectively treated in a solution comprising:
  362.5 ml distilled water
  14.05 g cupric sulphate
  94 ml propionic acid
  80 ml sulphurous acid
  40 ml formic acid
  50 ml formalin
  20 g cupric chloride
  25 g 20-20-20 N-P-K fertilizer
  65.5 g citric acid
  40 ml DBE (Dibasic ester—an esterified waste by-product of acrylic manufacture from Dupont Canada Ltd.)
  2.7 g magnesium sulphate
  5.4 g sodium sulphite
  229.5 ml 2-propanol
  0.2 g butylated hydroxytoluene
  40.5 ml ethylene glycol
  13.5 ml glycerol.

Coniferous needles such as white spruce, balsam, white cedar and junipers and other leaves such as ferns and holly may be most effectively treated in a solution comprising:
  362.5 ml distilled water
  14.05 g cupric sulphate
  104 ml propionic acid
  100 ml sulphurous acid
  50 ml formic acid
  50 ml formalin
  20 g cupric chloride
  25 g 20-20-20 N-P-K fertilizer
  65.5 g citric acid
  5.4 g sodium sulphite
  229.5 ml 2-propanol
  0.2 g butylated hydroxytoluene
  40.5 ml ethylene glycol
  13.5 ml glycerol.

EXAMPLE

After treating selected leaves in an appropriate solution as noted hereinabove, under the standard conditions as also noted, the resultant treated leaves were evaluated for colour and texture. The results are tabulated in Table 1 below:

TABLE 1

| Specimens | Solution 1 | Solution 2 | Solution 3 |
|---|---|---|---|
| mosses, forest | excellent c & t | — | — |
| lichens | excellent c & t | — | — |
| sword ferns | very good c & t | — | — |
| grasses | very good | — | — |

TABLE 1-continued

| Specimens | Solution 1 | Solution 2 | Solution 3 |
|---|---|---|---|
| | c & t | | |
| asparagus ferns | very good | — | — |
| mosses, sphagnum | good | — | — |
| Oregon grape | good | — | — |
| salal | poor | O.K. for present | — |
| arbutus | poor-fair | — | — |
| black spruce | good | — | — |
| white spruce | good | — | good |
| balsam | poor | — | good |
| geranium | fair | — | — |
| holly | — | — | good |
| sugar maple | — | — | — |
| silver maple | — | — | — |
| birch | — | — | — |
| white cedar | — | — | good |
| greenhouse ferns | — | — | good |
| junipers | — | — | good |
| red oak | — | — | — |
| basswood | — | — | — |
| cat-tails | — | — | — |
| beech | — | — | — |
| flowering crab | — | — | — |
| elm | — | — | — |
| larch | poor | — | — | c = colour
t = texture

We claim:

1. A solution, for the preservation of naturally green coloured plant tissues, consisting essentially of: 35–45% by volume water, 20–30% 2-propanol, 5–12% propionic acid, 5–10% sulphurous acid, 5–10% formalin, 2.5–5% formic acid, 1–5% ethylene glycol, a selected amount of (a) at least one cupric salt selected from the group consisting of cupric sulphate, cupric chloride, cupric carbonate, cupric acetate and cupric nitrate, (b) citric acid, (c) sodium phosphate, (d) sodium sulphite, (e) DBE, (f) 20-20-20 fertilizer, (g) magnesium sulphate, (h) glycerol, (i) butylated hydroxytoluene.

2. A solution as claimed in claim 1 comprising:
   425 ml distilled water
   14.2 g cupric sulphate
   56 ml propionic acid
   75 ml sulphurous acid
   25 ml formic acid
   100 ml formalin
   80 g cupric chloride
   10 g 20-20-20 N-P-K fertilizer
   42 g citric acid
   2.8 g magnesium sulphate
   25 ml acetic acid
   10 g cupric acetate
   10 g cupric nitrate
   10 g sodium phosphate (dibasic)
   5.6 g sodium sulphite
   238 ml 2-propanol
   0.21 g butylated hydroxytoluene
   42 ml ethylene glycol
   14 ml glycerol.

3. A solution as claimed in claim 1 comprising:
   362.5 ml distilled water
   14.05 g cupric sulphate
   94 ml propionic acid
   80 ml sulphurous acid
   40 ml formic acid
   50 ml formalin
   20 g cupric chloride
   25 g 20-20-20 N-P-K fertilizer
   65.5 g citric acid
   40 ml DBE
   2.7 g magnesium sulphate
   5.4 g sodium sulphite
   229.5 ml 2-propanol
   0.2 g butylated hydroxytoluene
   40.5 ml ethylene glycol
   13.5 ml glycerol.

4. A solution as claimed in claim 1 comprising:
   362.5 ml distilled water
   14.05 g cupric sulphate
   104 ml propionic acid
   100 ml sulphurous acid
   50 ml formic acid
   50 ml formalin
   20 g cupric chloride
   25 g 20-20-20 N-P-K fertilizer
   65.5 g citric acid
   5.4 g sodium sulphite
   229.5 ml 2-propanol
   0.2 g butylated hydroxytoluene
   40.5 ml ethylene glycol
   13.5 ml glycerol.

5. A process for preserving naturally green coloured plant tissues comprising immersing said tissues in a solution comprising: 35–45% by volume water, 20–30% 2-propanol, 5–12% propionic acid, 5–10% sulphurous acid, 5–10% formalin, 2.5–5% formic acid, 1–5% ethylene glycol, a selected amount of (a) at least one cupric salt selected from the group consisting of cupric sulphate, cupric chloride, cupric carbonate, cupric acetate and cupric nitrate, (b) citric acid, (c) sodium phosphate, (d) sodium sulphite, (e) DBE, (f) 20-20-20 fertilizer, (g) magnesium sulphate, (h) glycerol, (i) butylated hydroxytoluene.

6. A process as claimed in claim 5 for preserving salal leaves wherein said solution comprises:
   362.5 ml distilled water
   14.05 g cupric sulphate
   94 ml propionic acid
   80 ml sulphurous acid
   40 ml formic acid
   50 ml formalin
   20 g cupric chloride
   25 g 20-20-20 N-P-K fertilizer
   65.5 g citric acid
   40 ml DBE
   2.7 g magnesium sulphate
   5.4 g sodium sulphite
   229.5 ml 2-propanol
   0.2 g butylated hydroxytoluene
   40.5 ml ethylene glycol
   13.5 ml glycerol.

7. A process as claimed in claim 5 for preserving leaves selected from the group comprising mosses, lichens and ferns wherein said solution comprises:
   425 ml distilled water
   14.2 g cupric sulphate
   56 ml propionic acid
   75 ml sulphurous acid
   25 ml formic acid
   100 ml formalin
   80 g cupric chloride
   10 g 20-20-20 N-P-K fertilizer
   42 g citric acid
   2.8 g magnesium sulphate
   25 ml acetic acid
   10 g cupric acetate 10 g cupric nitrate
10 g sodium phosphate (dibasic)
5.6 g sodium sulphite
238 ml 2-propanol
0.21 g butylated hydroxytoluene
42 ml ethylene glycol
14 ml glycerol.

8. A process as claimed in claim 5 for preserving leaves selected from the group comprising white spruce, balsam, holly, white cedar and juniper, wherein said solution comprises:
362.5 ml distilled water
14.05 cupric sulphate
104 ml propionic acid
100 ml sulphurous acid
50 ml formic acid
50 ml formalin
20 g cupric chloride
25 g 20-20-20 N-P-K fertilizer
65.5 g citric acid
5.4 g sodium sulphite
229.5 ml 2-propanol
0.2 g butylated hydroxytoluene
40.5 ml ethylene glycol
13.5 ml glycerol.

* * * * *